US008845653B2

(12) United States Patent  (10) Patent No.: US 8,845,653 B2
Harper et al.  (45) Date of Patent:  Sep. 30, 2014

(54) FORCEPS

(75) Inventors: Dale Steven Harper, Cardiff (GB);
John Aiden Nally, Birmingham (GB);
David John Townsend, Solihull (GB);
Khaled Mostafa Kam Ismail, Market Drayton (GB)

(73) Assignee: Pro Medical Innovations Limited, Cardiff (GB)

( * ) Notice: Subject to any disclaimer, the term of this patent is extended or adjusted under 35 U.S.C. 154(b) by 458 days.

(21) Appl. No.: 13/123,921

(22) PCT Filed: Oct. 13, 2009

(86) PCT No.: PCT/GB2009/002458
§ 371 (c)(1),
(2), (4) Date: Jun. 6, 2011

(87) PCT Pub. No.: WO2010/043860
PCT Pub. Date: Apr. 22, 2010

(65) Prior Publication Data
US 2011/0245865 A1  Oct. 6, 2011

(30) Foreign Application Priority Data

Oct. 18, 2008  (GB) ................................ 0819128.0
May 13, 2009  (GB) ................................ 0908237.1

(51) Int. Cl.
*A61B 17/44*  (2006.01)
*A61B 19/00*  (2006.01)
*A61B 17/00*  (2006.01)

(52) U.S. Cl.
CPC ........... *A61B 17/44* (2013.01); *A61B 2019/464* (2013.01); *A61B 2017/00477* (2013.01); *A61B 17/442* (2013.01); *A61B 2017/445* (2013.01); *A61B 2017/00876* (2013.01)
USPC ........................................ 606/122; 606/208

(58) Field of Classification Search
USPC ............ 606/119–124, 174, 205–211; 24/303; 338/2–6; 73/862.635, 862.642
See application file for complete search history.

(56) References Cited

U.S. PATENT DOCUMENTS

| 3,389,459 | A | * | 6/1968 | Russell | 29/621.1 |
| 3,785,381 | A | * | 1/1974 | Lower et al. | 606/122 |
| 4,770,049 | A | * | 9/1988 | Jones et al. | 73/862.635 |
| 5,649,934 | A | * | 7/1997 | Smeltzer et al. | 606/122 |
| 5,674,243 | A | * | 10/1997 | Hale | 606/205 |
| 5,800,440 | A | * | 9/1998 | Stead | 606/104 |
| 6,425,899 | B1 | | 7/2002 | Biehl | |
| 6,582,451 | B1 | | 6/2003 | Marucci et al. | |
| 6,666,876 | B2 | * | 12/2003 | Kawai et al. | 606/205 |
| 7,014,642 | B1 | * | 3/2006 | Perone | 606/122 |

(Continued)

FOREIGN PATENT DOCUMENTS

| FR | 2858406 | 2/2005 |
| WO | 2004069030 | 8/2004 |
| WO | 2004108010 | 12/2004 |
| WO | 2009089614 | 7/2009 |

*Primary Examiner* — Kathleen Holwerda
(74) *Attorney, Agent, or Firm* — Lowe Hauptman & Ham, LLP

(57) ABSTRACT

The invention provides a forceps system comprising a pair of forceps members and force measurement means operable to measure compressive and traction forces exerted by the forceps when in use, and to output measurement signals indicative of such forces. Also provided is a method of measuring the compressive and traction forces exerted by a forceps system when in use.

9 Claims, 5 Drawing Sheets

(56) References Cited

U.S. PATENT DOCUMENTS

| | | |
|---|---|---|
| 7,426,872 B2 | 9/2008 | Dittmar et al. |
| 2003/0220655 A1 | 11/2003 | Rose |
| 2007/0078484 A1 * | 4/2007 | Talarico et al. ............... 606/205 |
| 2009/0188094 A1 | 7/2009 | Cunningham et al. |

* cited by examiner

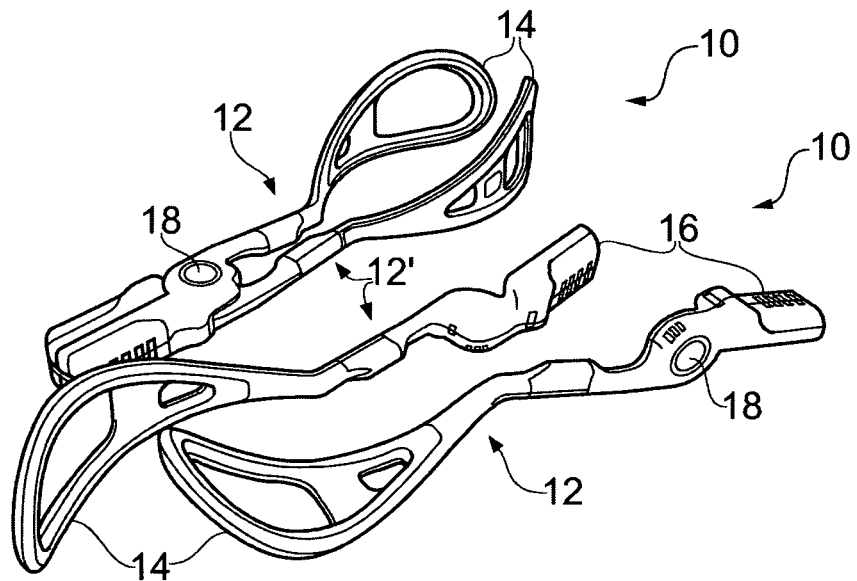
FIG. 1
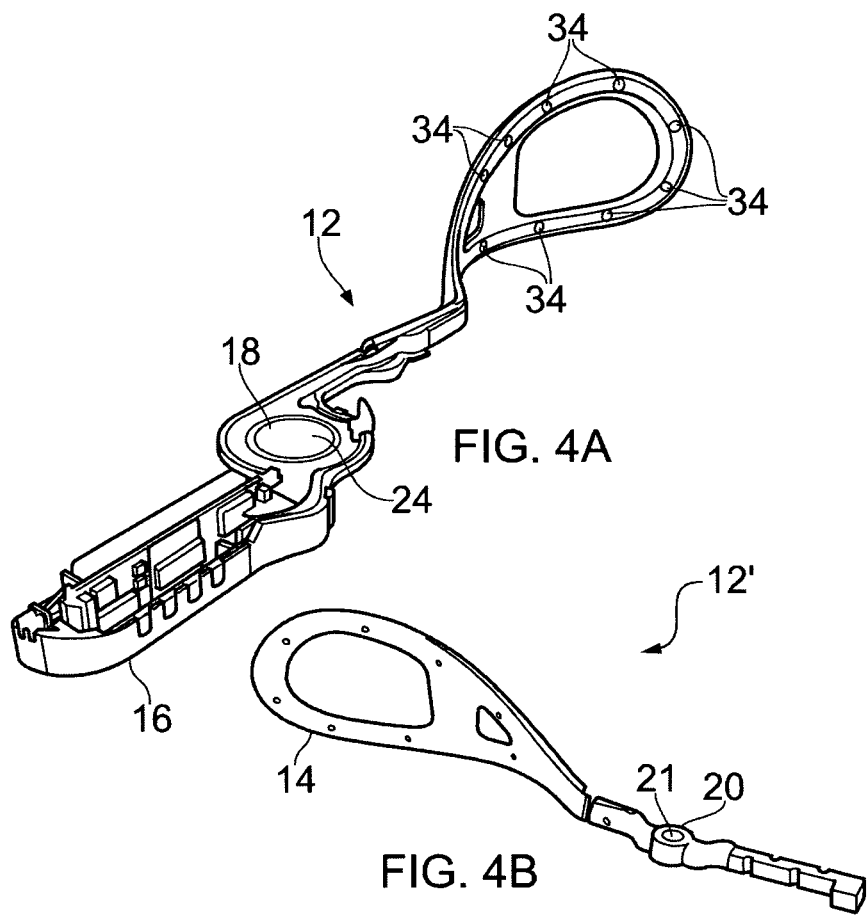
FIG. 4A
FIG. 4B

FORCEPS

RELATED APPLICATIONS

The present application is based on, and claims priority from, GB Application Number 0819128.0, filed Oct. 18, 2008, GB Application Number 0908237.1, filed May 13, 2009, and PCT Application Number PCT/GB09/002458, filed Oct. 13, 2009, the contents of which are hereby incorporated by reference herein in their entireties.

BACKGROUND TO THE INVENTION

The present invention relates to a forceps system for the measurement of compression and traction forces, including the measurement of compression and traction forces exerted upon a fetal head during instrumental delivery.

Forceps are well known for grasping objects by applying pressure to the object to retain it within the forceps then applying force in the desired direction of movement of the object. For example, forceps are used to grasp crucibles of molten metal in order to remove them from a furnace and the like. Similarly, forceps are often used during difficult births to assist with the birthing process by grasping the head of the baby and applying a force in the birthing direction to assist with the delivery of the baby through the birthing canal.

Depending on the intended use of the forceps, the forceps blades are typically designed to correspond to the contours of the object to be grasped. For example, the forceps for use in assisting childbirth have blades which are contoured appropriately to receive a baby's head therebetween during use.

Conventional obstetrical forceps work by engaging the head of the baby whilst still inside the body of the mother. The forceps are then used to either turn the baby's head to a new position to allow natural childbirth to progress more easily, and/or to exert tractional or rotational force on the baby's head in order to pull the baby through the birth canal during delivery. The amount of traction or pressure applied to the skull of the baby during this delivery process is extremely important—sufficient traction or pressure needs to be applied to achieve the desired movement of the baby however, too much traction or pressure can result in injuries to the baby, including brain, scalp and/or facial injuries. The amount of force applied is subject to the clinical judgement of the medical expert operating the forceps and so there is no reliable way to ensure that excessive force is not applied and that the potential complications for the baby are avoided.

An alternative device which may be used to assist childbirth is the vacuum extractor. With vacuum extrusion there is means available to measure the operational forces used and exerted during the birthing process. These forces are then applied within 'safe operating parameters' as a way of preventing excessive force application to the head of the baby during childbirth. However, vacuum extrusion carries its own risks and complications, including but not limited to haematoma (a blood collection in the scalp). Although this type of injury is typically resolved without further problems, occasionally life threatening injuries such as subgaleal (subaponeurotic) hematoma, retinal haemorrhages or intracranial haemorrhage may occur.

There is therefore a need for a device which is simple for a medical expert to use, but which allows the accurate measurement of the forces applied by the medical expert to the baby's head during the birthing process in real time so that the medical expert can avoid inflicting injuries on the baby during the assisted delivery.

SUMMARY OF THE INVENTION

The present invention seeks to address the problems of the prior art.

Accordingly, a first aspect of the present invention provides a forceps system comprising a pair of forceps members; and force measurement means operable to measure compressive and traction forces exerted by the forceps when in use, and to output measurement signals indicative of such forces.

By measuring both the compressive and traction forces in real time, it is possible for the operator of the forceps system to know at all times the forces being applied and to adjust the applied forces to avoid the forces being applied from becoming excessive and resulting in damage to the object being held by the forceps system. This invention is particularly, although not exclusively, intended for use during the forceps-assisted childbirth. Thus, being able to monitor the forces being applied to the head of the baby in real time during this process assists in prevention of potential injury to the head and neck of the baby during delivery.

In one embodiment, the forceps members are pivotally engaged with one another. However, it will be appreciated that any other suitable inter-relationship between the forceps members allowing the desired relative movement may be used as an alternative such as, but not limited to, hinged engagement, sliding engagement or rotational engagement.

In a further embodiment, at least one of the forceps members is provided with a pressure sensor operable to measure compressive forces.

Preferably, the pressure sensor is located on a surface of the forceps member opposing the other forceps member. This way, the pressure sensors are located in such a manner so as to detect and measure the force applied by each forceps member at the object being gripped therebetween, for example, the head of the baby during delivery.

The pressure sensor may be selected from the group comprising microelectromechanical (MEM) piezoresistive force sensors, quantum tunnelling composite (QTC) sensors and force sensing resistors (FSRs).

The or each forceps member may comprise a blade portion and a handle portion with a deformable O-ring located between the blade portion and the handle portion. Thus, any deflection of the blade portion relative to the handle portion will result in deformation of the deformable O-ring.

Preferably, the forceps blade portions are mirror images of one another. As the contours of each forceps member mirror one another, this allows equal force to be applied through each forceps member to the object gripped there between.

Preferably, the O-ring is located adjacent the point of pivotal engagement of the two forceps members and may be further provided with a strain gauge mounted on the deformable O-ring. In this way, any deformation of the O-ring will be detected by the strain gauge and thus the traction forces through the forceps system may be detected and measured. More preferably, the O-ring is located between the point of pivotal engagement and the forceps blade portions.

It is to be appreciated that although an embodiment of the present invention utilises a deformable O-ring in the measurement of traction forces through the forceps system, any other suitable means of measuring such traction forces may be employed in addition to or as an alternative to the deformable O-ring feature.

In a further embodiment, an array of strain gauges is mounted adjacent the point of pivotal engagement of the forceps members. By using an array of strain gauges, a more accurate measure of the traction forces through the forceps system may be made.

Preferably, one or more of the strain gauges may be mounted on an external cylindrical surface of the deformable O-ring. In this way, the or each strain gauge will be located at a region of the deformable O-ring that will experience the most deformation during the application of traction forces through the forceps system and thus the or each strain gauge will be located in a position that allows the most sensitive detection of force-induced deformation of the deformable O-ring.

In a further embodiment, the forceps members are held together by magnetic forces at the point of pivotal engagement between the pair of forceps members. This is achieved by the provision of opposing magnets of opposite polarity, one located on each forceps member at the point of pivotal engagement. The provision of magnetic inter-engagement facilitates smooth pivotable relative movement between the forceps members. Furthermore, the use of the magnetic inter-engagement allows simple disengagement of the forceps members from one another when not in use to facilitate cleaning and/or sterilisation of the forceps members. The simple separation of the forceps members means that the conventional problem of cleaning the forceps system at hinge points is avoided. A further advantage of the use of magnets is that the relative movement of forceps members is possible without any deformation of the deformable O-ring. Thus, any detected deformation of the deformable O-ring is as a result of traction forces through the forceps system and/or compressive forces through respective forceps handle portions.

A further advantage of the use of magnetic inter-engagement in a forceps system for use in forceps-assisted childbirth is that it assists with the reliable inter-engagement of the forceps members with one another during the engagement process.

Preferably, the region of pivotal engagement of each forceps member is provided with contours to assist the separation of the forceps members from one another during use. The contours preferably comprise a ramped region whereby rotation of the forceps members relative to one another causes each forceps member to rise up the ramp of the opposing forceps member, thereby separating the forceps members from one another at the point of pivotal engagement. This assists in overcoming the opposing magnetic forces and facilitating ease of separation of the forceps members from one another.

Preferably, at least a portion of the forceps members comprise a resilient material. The resilient material may be an elastomeric polymer material, such as a biocompatible elastomeric material, although it will be appreciated that any other suitable resilient material may be used in combination with, or as an alternative to, the elastomeric polymer material.

A further aspect of the present invention comprises a method of measuring the compressive and traction forces exerted by a forceps system when in use, the method comprising the steps of:
a. Providing a forceps system having a pair of forceps and force measurement means operable to measure compressive and traction forces exerted by the forceps;
b. Locating the forceps around an object and applying compression and/or traction forces to the object via the forceps;
c. Transmitting the compressive and traction force measurements to a controller;
d. Outputting said measurements to a user in real time during use of the forceps.

The compression and/or traction forces applied at step b above may be in addition to additional forces applied to the object where the object is a foetal head and the forceps system is being used during forceps-assisted delivery.

The outputting of the measured force data may involve the transmission of the data, either by wireless technology (including but not restricted to Bluetooth technology, radio frequencies and infra red technology) or by cable transmission, to a controller such as a computer or the like. The received force data may be visualised by means of a viewer or display unit such as but not restricted to a computer screen or the like. In addition, the controller may be provided with alarm means, such as an audible and/or visual alarm signal or the like, to indicate when the received force measurements fall outside of a predetermined range.

The controller may record the received force data over time during the procedure of use such that a record of the procedure is available for reference after the event is complete. The recorded force data may optionally be archived, analysed and subsequently used to develop and implement pre-emptive warning systems for use during future forceps system operations.

BRIEF DESCRIPTION OF THE DRAWINGS

Embodiments of the present invention will now be described, by way of example only, and with reference to the accompanying drawings, in which:

FIG. 1 is a perspective view of an embodiment of two forceps systems; one in an engaged configuration and one in an unengaged configuration;

FIG. 4A is a view of the electronic component of a forceps system of FIG. 1;

FIG. 4B is a view of a further component of the forceps system of FIG. 1;

DETAILED DESCRIPTION OF THE INVENTION

Figure 6:
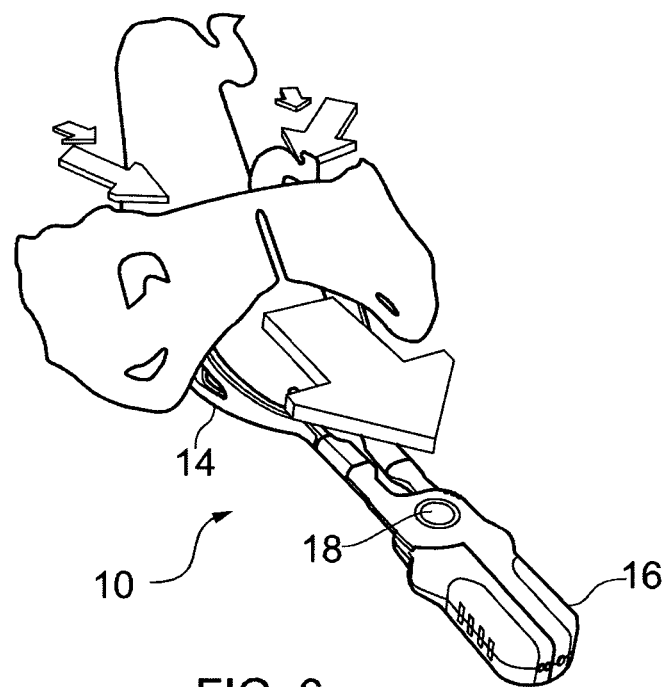
FIG. 6 illustrates the forceps of FIG. 1 in use in an obstetric situation.
Figure 2:
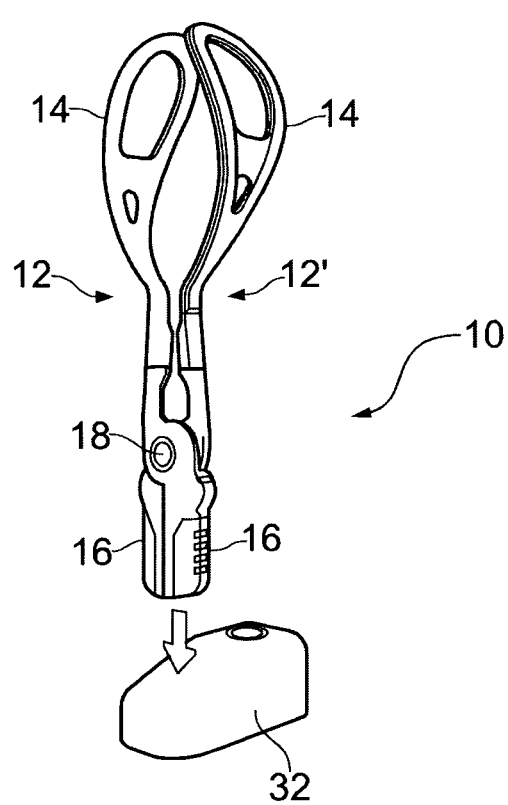
FIG. 2 is a perspective view of an embodiment of the forceps system of FIG. 1 together with an associated charging unit.

FIG. 1 shows an embodiment of a forceps system 10 according to a first aspect of the present invention with the forceps members 12, 12' in an assembled state and also a further two forceps members 12, 12' in the unassembled state. FIGS. 4A and 4B show components of forceps member 12. The forceps system 10 of FIG. 1 is intended for obstetric use during forceps delivery.

Each of forceps members 12, 12' comprises a blade portion 14 at a first end thereof and a respective handle portion 16 at an opposing end thereof, with a respective deformable element in the form of a deformable O-ring 20. The deformable O-ring 20 is composed of a resilient material which deforms under applied force exerted through the forceps system 10.

It will be appreciated that blade portion 14 of forceps member 12 is a mirror image of blade portion 14 of forceps member 12'. The opposing surfaces of respective forceps blade portions 14, which contact and grip the object to be held therebetween, are composed at least in part of an elastomeric polymer which provides a resilient contact surface for gripping the head of a baby during the birthing process. However, it will be appreciated that any suitably resilient material may be used in addition to, or as an alternative to, such an elastomeric material.

Deformable O-ring 20 is annular and an array of strain gauges 21 is provided on the external cylindrical surface of the deformable O-ring 20. Each strain gauge 21 within the array is position to detect deformation of the adjacent O-ring region when traction force is applied through the forceps system 10. Thus, the provision of such an array of strain gauges 21 on the outer cylindrical surface of the deformable O-ring 20 allows for traction force identification and measurement on a plurality of planes.

In addition, the array of strain gauges 21 is also able to identify and measure compressive force applied across the handle portion 16 due to the resultant deformation of the deformable O-ring on application of such compressive force to bring the blade portions 14 of respective forceps members 12, 12' towards one another, in use.

When the forceps system 10 is assembled the two forceps members 12, 12' are position such that respective blade portions 14 of forceps members 12 and 12' are facing one another and the two forceps members 12, 12' are pivotally engaged with one another at pivot point 18, such that respective deformable O-rings become aligned.

Each of forceps members 12 and 12' are provided with a magnet 24, each magnet being of opposite polarity such that respective magnets 24 are attracted to one another. In use, forceps members 12, 12' are held in engagement at pivot point 18 under the magnet attractive forces of opposing magnets 24.

Figure 7:
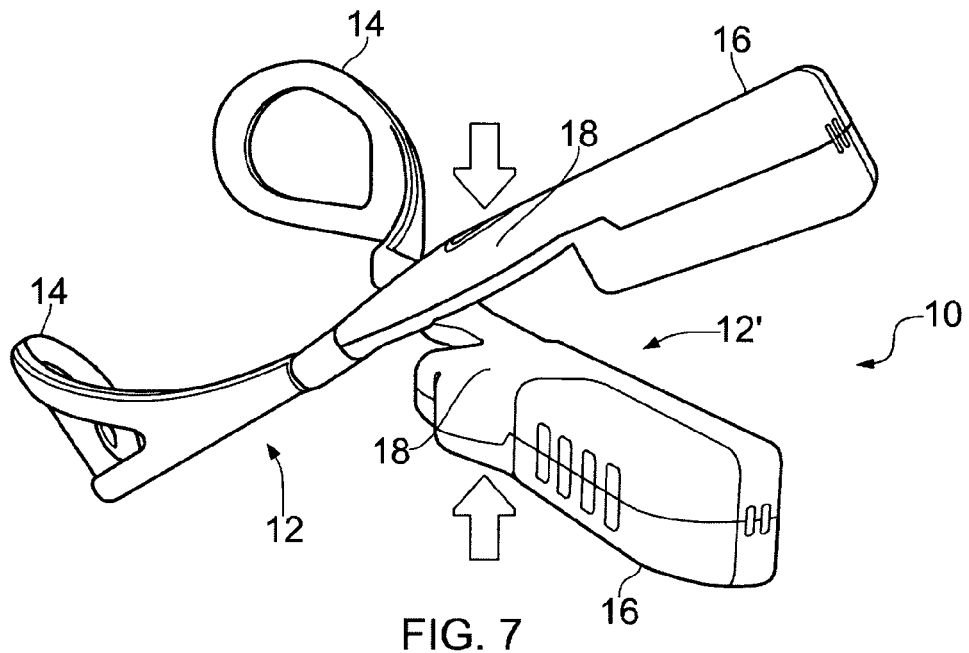
FIG. 7 is a perspective view of the forceps system of FIG. 1 illustrating the range of movement possible using magnetic forces to engage the pair of forceps members with one another in use.
Figure 5:
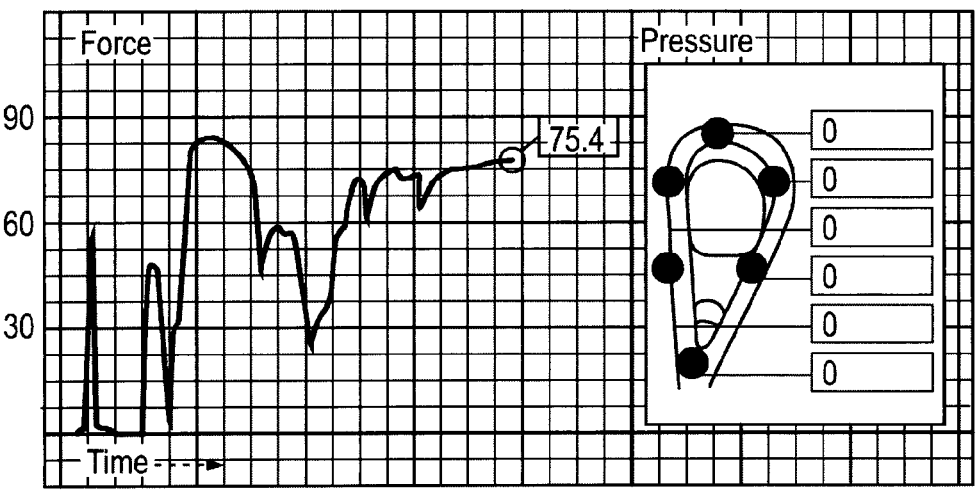
FIG. 5 is a graphical representation of a display output based on measurements taken by sensors at various positions around the forceps blade of a forceps member of the forceps system of FIG. 1.
Figure 5:
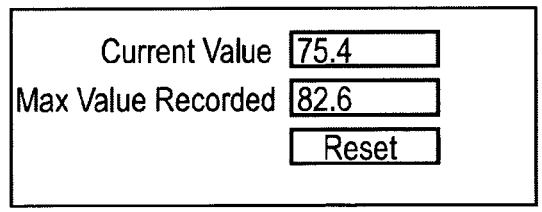
Figure 9:
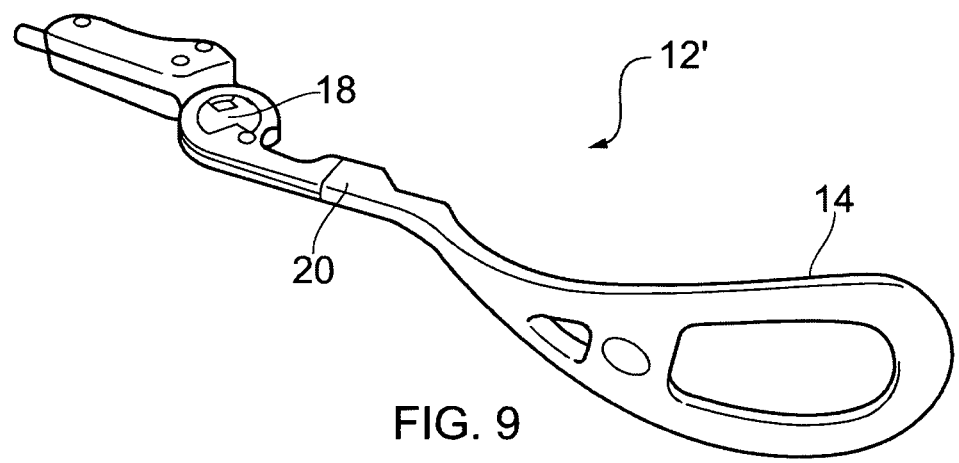
FIG. 9 is a partial perspective view of the embodiment of FIG. 1 showing the locations of the inter-engagement region at one of the pair of forceps members.

Thus, in use, forceps members 12, 12' are pivotable relative to one another about pivot point 18 but are held together at pivot point 18 under magnetic forces. FIG. 7 shows the two forceps members 12, 12' being brought together such that the magnets 24 are brought into contact with one another. The forceps members 12, 12' are brought together in the direction of the arrows shown in FIG. 7. Disengagement of this pivot is through mechanical means and contrary to the magnetic engagement forces—ensuring definite and/or intended engagement and disengagement of the forcep members.

Figure 3:
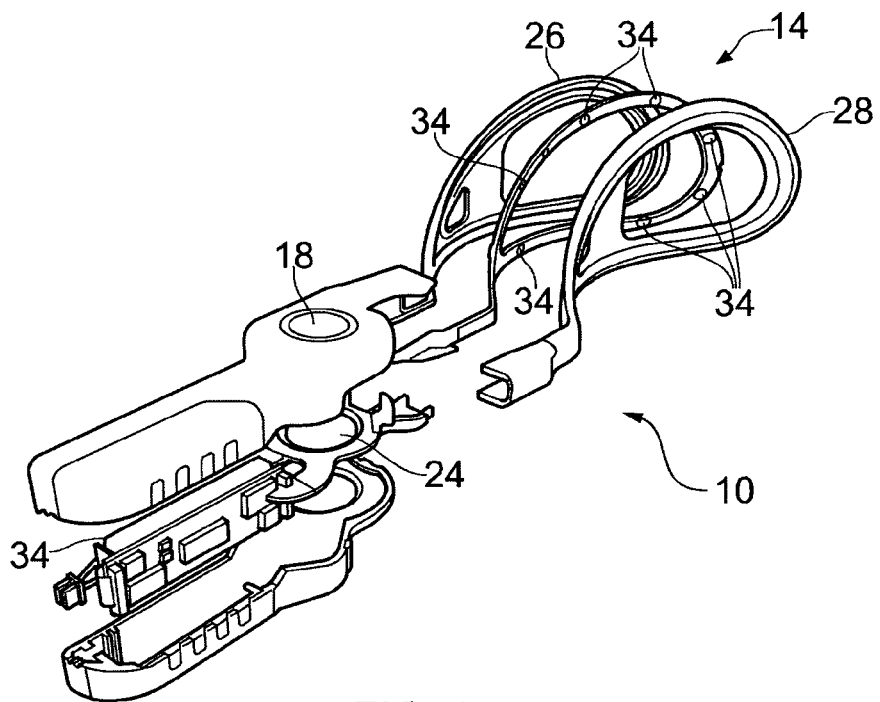
FIG. 3 is an exploded view of a forceps member of the forceps system of FIG. 1.

FIG. 3 shows an exploded view of forceps member 12 with each of the component parts indicated. As can be seen, blade portion 14 is composed of an outer blade portion 26 and inner blade portion 28. The inner and outer blade portions 26, 28 are metal substructure with a plastic over-moulding. When located in position relative to one another they create a hollow structure within which is housed the internal electronics, including sensors 34.

Inner and outer blade portions 26, 28 are ultrasonically welded together to create two separate forceps members 12, 12' which are mirror images of one another with the internal electronics (including sensors 34) securely located therebetween.

Sensors 34 are MEM sensors and are positioned to detect compression forces exerted by the forceps blades on an object being gripped, during use. The forceps system shown in the figures is intended for use in the birthing process to facilitate a forceps delivery. Therefore, the forceps blade portions 14 are contoured to correspond to the contours of a baby's skull.

The sensors 34 are therefore positioned to measure the compression forces applied by the forceps blade portions 14 to the baby's skull during the forceps delivery process.

The compression and traction forces detected and measured by sensors 34 and the array of strain gauges are regulated and calibrated within the handle portion 16 of the forceps system 10 by means of a processing card (not shown) through a series of amplification.

However, it will be appreciated that the signal amplification, calibration and processing may take place by any suitable means available to the skilled person. For example, the signal amplification, calibration and processing may occur on a small chip board adapted to be received within a conventional PCMCIA card slot or the like. Alternatively, the amplification and/or calibration/processing may take place on a PCI card within a PC, in a separate processing unit or even on a single chip housed within the forceps system itself.

Figure 8:
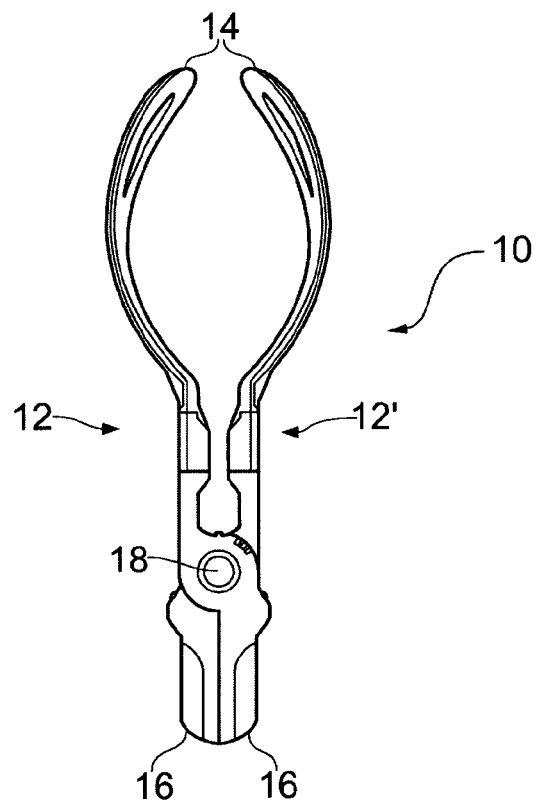
FIG. 8 is a further view of the forceps system of FIG. 1 in the fully closed position.

The detected force data is then wirelessly transmitted to a controller such as a computer or the like using Bluetooth technology. It will be appreciated that alternative wireless communication technologies may be applied. Alternatively, wired communication may be used. A wireless embodiment of a forceps system 10 in accordance with the present invention is shown in FIG. 8. However, wireless communication methods have the advantage that the forceps system mobility is unhampered by the presence of the tethered connection to the controller which processes the detected force data.

However, the detection and amplification of the forces detected through the forceps system 10 and the onward transmission of the collected data to a controller for outputting and/or visualising the data for real time viewing by a user requires an energy source.

This may be achieved in several conventional ways. For example, the embodiment of a forceps system 10 shown in FIG. 1 is rechargeable and in FIG. 3 is shown being inserted into it accompanying recharger unit 32, the forceps system 10 being moved into position relative to the charger in the direction of the arrow shown. Contacts provided on the outer surface of the handle portion 16 of the forceps system make contact with contacts provided at the recharger unit 32. The recharger unit 32 may provide power to recharge a battery within the handle portions 16 of the forceps members 12 of forceps system 10. The recharger unit 32 may be plugged in to the mains as a source of power. Alternatively, it will be appreciated that the recharger unit may include a battery which donates power to the rechargeable battery in the forceps system. The recharger unit 32 acts as a docking station for the forceps system 10 when not in use, thus the docked forceps system 10 will be in a suitable state for use when required.

FIG. 6 shows the forceps system 10 in use during a forceps delivery procedure. The forceps system 10 is guided into position such that opposing forceps blade portions 14 are position on opposing sides of the head of the baby. Once in position, compressive forces are applied by a use through the handle portions 16 thereby gripping the head of the baby between the opposing forceps blade portions 14. In addition, during the delivery process, cervical forces may be applied from the mother's cervical skeleton and as a result of the muscular contractions which result in compressive forces being application to the forceps system. These forces are independent of the forces applied by a user to the forceps system during use. However, these cervical forces will also be included within the measured forces detected by the forceps system during use due to their compressive effect on the deformable O-ring 20 and the compressive force on the MEM's sensors (or other). It is the collective value which is of primary importance with this system.

The compressive forces are detected by the sensors 34 located at the forceps blade portions 14, the measured force data being amplified then wirelessly transmitted to the controller where the data is visualised in real time for viewing by a user. In this way, the user may be aware at all times of the compressive forces being applied to the head of the baby and can therefore avoid the application of excessive force that may result in injury to the baby's skull.

Once the baby's head is gripped between the blade portions 14 of the forceps system 10, the user applies traction force to the head of the user (in tandem with the natural contraction forces of the mother) in the direction of delivery. Any resistance to being pulled in the direction of delivery results in traction forces being applied through the forceps system 10 causing deformation of the deformable O-ring 20. The traction forces are detected and measured by the array of strain gauges positioned at the deformable O-ring 20, amplified, and then transmitted wirelessly to the controller where the data is visualised in real time for viewing by the user. In this way, the user may be aware at all times of the traction forces being applied through the forceps system 10 and can therefore avoid the application of excessive force that could cause injury to the baby's skull. The inverse of this is also possible whereby a negative reading is generated when a pushing force is applied upon the fetal head. This is of even greater danger than the primary force or compressive/traction force. The system also accommodates measurement and warnings of this.

Thus, by detecting forces using both sensors 34 and the array of strain gauges, the forceps system 10 of the present invention measures both the traction (and potential pushing) force exerted by the user and the compressive forces exerted by the combined traction force of the user, the contraction force of the mother and the natural resistance formed by the shape of the pelvis during the delivery procedure.

The forceps system 10 may be provided with a movement switch (not shown) which may be embedded in the handle portion 16 of one or each forceps member 12, 12' such that movement of the forceps system 10 activates force detection view the sensors 34 and strain gauge array 22. Alternatively, the forceps may switch on automatically if mains powered simply by being plugged into the mains. Where a wireless version is used, a warning indicator, such as an LED display or the like, may be provided to indicate when battery power reaches a predetermined threshold level.

Finally, the handle portion 16 may be tailored ergonomically to suit the requirements of a user by the selective use of a two-shot injection moulding technique to provide ergonomic grip areas within the contours of the handle portion 16 thereby increasing the comfort for the user and ultimately the ease of use of the forceps system 10 in practice.

Although aspects of the invention have been described with reference to the embodiment shown in the accompanying drawings, it is to be understood that the invention is not limited to the precise embodiment shown and that various changes and modifications may be effected without further inventive skill and effort. For example, it will be appreciated that although the exemplified forceps system is intended for forceps delivery during the birthing process, a forceps system in accordance with the present invention may be used for many other purposes beyond human obstetrics and gynaecology, including but not restricted to veterinary, medical, and surgical applications, and is not restricted to use during the delivery process. If desired, the contours of the blade portions may be modified to correspond to the object to be gripped therebetween such that the pressure sensors are located adjacent points of contact of the blade portions with the object to be gripped therebetween.

The invention claimed is:

1. A forceps system comprising:
a pair of forceps members; and
force measurement means operable to measure compressive and traction forces exerted by the forceps members when in use, and to output measurement signals indicative of such forces,
wherein a forceps member comprises a blade portion and a handle portion,
wherein the force measurement means comprises a deformable O-ring located between the blade portion and the handle portion, and
wherein a strain gauge is mounted on the deformable O-ring,
wherein at least one of the forceps members comprises a pressure sensor operable to measure compressive forces.

2. A forceps system according to claim 1 wherein the pressure sensor is located on a surface of the forceps member opposing the other forceps member.

3. A forceps system according to claim 1, wherein the pressure sensor is selected from the group comprising microelectromechanical piezoresistive force sensors, quantum tunneling composite sensors and force sensing resistors.

4. A forceps system according to claim 1, wherein the O-ring is located adjacent a point of pivotal engagement of the two forceps members.

5. A forceps system according to claim 1, wherein an array of strain gauges is mounted on the deformable O-ring.

6. A forceps system according to claim 5, wherein in the array of strain gauges is mounted on an external cylindrical surface of the deformable O-ring.

7. A forceps system according to claim 1, wherein the forceps members are engaged with one another by magnetic forces at a point of pivotal engagement between the pair of forceps members.

8. A forceps system according to claim 1, wherein at least a portion or the forceps members comprise a resilient material.

9. A forceps system according to claim 8, wherein the resilient material is an elastomeric polymer material.

* * * * *